United States Patent [19]
Miyauti et al.

[11] Patent Number: 5,948,692
[45] Date of Patent: *Sep. 7, 1999

[54] METHOD AND MEASUREMENT KIT FOR ASSAY OF NORMAL AGRECAN, AND METHOD FOR EVALUATION OF INFORMATIONS ON THE JOINT

[75] Inventors: Satoshi Miyauti; Katuyuki Horie, both of Musashimurayama, Japan

[73] Assignee: Seikagaku Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/687,406

[22] PCT Filed: Feb. 17, 1995

[86] PCT No.: PCT/JP95/00220

§ 371 Date: Aug. 2, 1996

§ 102(e) Date: Aug. 2, 1996

[87] PCT Pub. No.: WO95/22765

PCT Pub. Date: Aug. 24, 1995

[30] Foreign Application Priority Data

Feb. 19, 1994 [JP] Japan .................................... 6-059739

[51] Int. Cl.$^6$ .......................... G01N 33/53; G01N 33/566
[52] U.S. Cl. ............................................. 436/501; 435/7.1
[58] Field of Search .............................. 436/501; 435/7.1, 435/7.92; 530/387.5, 388.85, 389.1

[56] References Cited

U.S. PATENT DOCUMENTS

| | | | |
|---|---|---|---|
| 4,778,768 | 10/1988 | Heinegard et al. | 438/501 |
| 5,032,281 | 7/1991 | Nagamatsu et al. | 210/651 |
| 5,185,245 | 2/1993 | Heimer | 435/7.1 |

FOREIGN PATENT DOCUMENTS 2074727  11/1981  United Kingdom .

OTHER PUBLICATIONS

Heimer, R., Analytical Biochemistry 180:211–215, 1989.
Lohmander, et al., Arthritis and Rheumatism 36(2):181–189, Feb. 1993.
Dick Heinegard, et al., The Journal of Biological Chemistry, vol. 249, No. 13, Issue of Jul. 10, pp. 4250–4256, 1974.
Eugene J–M. A. Thonar, et al., Arthritis and Rheumatism, vol. 28, No. 12, pp. 1367–1376 (Dec. 1985).
A. Ratcliffe, et al., Annals of the Rheumatic Diseases, 1988; 47, 826–832.
New Biochemistry Experimental Handbook, vol. II, Proteoglycans and Glycosaminoglycans, pp. 449–455 (1991). English language abstract attached.
K. M. K. Bottomley, et al., Br. J. Pharmacol., 93, 627–635(1988).
R. W. Farndale, et al, Connect. Tissue Res., 9, 247–248 (1982).
Atherosclerosis, 98 (1993), pp. 179–191.
Collagen. Rel. Res, 2 (1982), pp. 45–60.
J. Immunol. Methods, 147 (1992), pp. 93–100.
Ann. Rteum. Dis 47 (1988), pp. 886–892.
Agents and Actions, 39 (1993), pp. 151–153.
Agents and Actions, 39 (1993), pp. 154–156.
Kongtawelert et al., Analytical Biochemistry; 178:367–372, 1989.
Extracellular Metabolism of Aggrecan, John D. Sandy, Articular Cartilage and Osteoarthritis, edited by K. Kuettner et al., Raven Press Ltd, New York, 1992.

*Primary Examiner*—Donna C. Wortman
*Assistant Examiner*—Brenda G. Brumback
*Attorney, Agent, or Firm*—Armstrong, Westerman, Hattori, McLeland & Naughton

[57] ABSTRACT

A method of assaying normal aglycans and an assaying kit therefor, which method comprises separating normal aglycans having an avidity for hyaluronic acid and present in a specimen from proteoglycans not having such an avidity and detecting only the normal aglycans. The separated normal aglycans are detected by the technique of detecting proteoglycans. The specimen is preferably a joint fluid originating in the joint as the target of judgement. A method of judging joint-related information comprises detecting information on the amount of normal aglycans in a specimen and the total amount of proteoglycans therein with the above method and kit, comparing the obtained information with the same type of information, which has been prepared in advance, on the amounts of the above-specified compounds in a joint fluid originating in a normal joint, and judging whether the obtained information is one pertinent to pathologic joints or one pertinent to normal joints on the basis of the presence or absence of any significant difference therebetween. The information pertinent to pathologic joints is classified into the one pertinent to arthrosis deformans, the one pertinent to rheumatoid arthritis, the one pertinent to traumatic arthritis, and the one pertinent to gout. The method and kit can be utilized for the biochemical diagnosis of joint diseases in the field of orthopedics. They can be utilized also for discriminating normal joints from pathologic joints, for grasping morbidity such as judgement on the type and prognosis of joint diseases, and for grasping the curative effects by determining the concentration of normal aglycan, the content of normal aglicans in the whole of proteoglycans, and so forth.

7 Claims, No Drawings

METHOD AND MEASUREMENT KIT FOR ASSAY OF NORMAL AGRECAN, AND METHOD FOR EVALUATION OF INFORMATIONS ON THE JOINT

FIELD OF THE INVENTION

This invention relates to the technique to utilize effectively the amount and quality of the cartilage matrix components released into synovial fluid as an important source of information on the metabolism of the matrix. This invention relates to the biochemical diagnosis of joint diseases in the field of orthopedics. In the concrete, this invention relates to the method and measurement kit for assay of normal aggrecan and to the method of evaluation of informations on the joint.

In more detail, this invention relates to the method for assay of normal aggrecan that can detect only normal aggrecan present in the specimen, to the measurement kit used for the assay, and to the method of evaluation of informations on the joint which can judge whether the joint is pathological or normal and determine the type of the pathological joint, based on the absence or presence of significant difference between the amount of normal aggrecan and that of total proteoglycan in the specimen and those in synovial fluid obtained from a normal joint.

In this invention, "normal aggrecan" means aggrecan that is capable of binding hyaluronan.

BACKGROUND OF THE INVENTION

It is well known that in a normal joint cartilage, a good balance is maintained between synthesis and destruction of the cartilage matrix, while in a pathological joint cartilage, destruction of the cartilage matrix has been accelerated irrespective of the type of the lesion. Degradation products of the cartilage matrix are first released into synovial fluid, then distributed into blood, and metabolized. Thus the amount and quality of each component of the cartilage matrix released into synovial fluid is an important source of information on the metabolism of the matrix. Proteoglycan, the main component of the cartilage matrix, is characterized by its being capable of forming an aggregate with hyaluronan to build up the huge mass of matrix structure together with the type II collagen in the cartilage matrix. The amount and quality of aggrecan, the main proteoglycan in the cartilage matrix, and its sugar chain, glycosaminoglycan, is a clue to know whether the destruction of the cartilage matrix has been accelerated.

The conventional method for assay of normal aggrecan consists in measurement of the amount of the hyaluronan-aggrecan aggregate isolated by ultracentrifugation (Heinegard, D., et al., J. Biol. Chem.,249, 4250 (1974)) and gel chromatography (Iwata, H., Shin Seikagaku Jikken Koza, Vol.3, Carbohydrates II, p.452–455, Apr. 15, 1991, published by Tokyo Kagaku Dojin Kabushiki Kaisha). The method is time-consuming and requires not a small amount of specimen.

Therefore an improved method for assay of normal aggrecan is now required; namely a method that requires a shorter time and a smaller amount of specimen. Also a method has been desired that can clarify the quantitative relationship between the change in normal aggrecan and the pathological state of a joint to judge whether the joint is pathological or normal and identify the type of the pathological joint, as the basis of diagnosis of arthritis or decision of a therapeutical plan.

As described above, proteoglycan in synovial fluid is useful as a marker molecule for diagnosis of arthritis, though in some types of arthritis the concentration of proteoglycan is lower than that in the normal joint; thus the increased concentration of proteoglycan does not always indicate that the joint is pathological.

DISCLOSURE OF THE INVENTION

This invention intends to provide a method for assay of a novel marker molecule for differentiation of a pathological joint from a normal one. Moreover this invention intends to provide a method for assay of a marker molecule which can differentiate different types of arthritis with different characteristics.

More particularly this invention intends to provide a convenient and very sensitive method and a measurement kit for assay of normal aggrecan in a specimen, especially of body fluid, and to provide a method for evaluation of informations on the joint using the method and the kit.

Even more particularly this invention intends to provide a method for assay of normal aggrecan that can detect only normal aggrecan present in the specimen, a kit for the assay, and a method for evaluation of informations on the joint which can judge whether the joint is pathological or normal, based on absence or presence of significant difference between the amount of normal aggrecan and that of total proteoglycan in the specimen and those in synovial fluid obtained from a normal joint.

In addition, this invention intends to provide a method for evaluation of the informations on the joint that can differentiate various types of pathological joints.

A component that is specific to the cartilage and reflects sensitively the metabolism of the matrix is useful as a marker molecule of a pathological joint. Aggrecan, the main proteoglycan in the cartilage matrix, and its sugar chain; glycosaminoglycans (sometimes abbreviated as GAGs hereinafter) are among the components of the cartilage matrix that possess the properties necessary for the marker molecules.

Proteoglycan is outlined in the following:

Proteoglycan is a general term given to the substances composed of a protein called core-protein and glycosaminoglycans covalently bound to the protein, which are present in the connective tissue, cellular membrane, etc., each having its own unique function.

The main proteoglycan in the cartilage is called aggrecan of which glycosaminoglycan chains are chondroitin sulfate and keratan sulfate.

The molecular weight of the core-protein of normal aggrecan is in the range of 200,000 to 300,000, containing two globular domains at the amino-terminal (G1 and G2 domains from the terminal) and one globular domain at the carboxyl-terminal (G3 domain). In the cartilage matrix, normal aggrecan is bound to hyaluronan at the G1 domain to form a huge aggregate. This aggregate is stabilized through the presence of a glycoprotein called link protein (molecular weight: 40,000 to 50,000) which can be bound both to normal aggrecan and to hyaluronan. There is a GAGs-bound region between the G2 and the G3 domains, where a number of chondroitin sulfate and keratan sulfate residues as well as N- or O-bound oligosaccharides are bound.

Chondroitin sulfate consists of repeating units of disaccharide consisting of N-acetylgalactosamine and glucuronic acid, and several disaccharide structures with different positions of the sulfate residue are known; the sulfate residue is linked at the 6-position of N-acetylgalactosamine (C6S) in about 90% of human aggrecan, and those with the sulfate residue linked at the 4-position (C4S) and those without sulfate residue (C0S) are found in this order of decreasing frequency. These structures are not present separately in different molecules of chondroitin sulfate but found in the same chondroitin sulfate molecule.

Keratan sulfate consists of repeating units of disaccharide consisting of N-acetylglucosamine and galactose. Two structure types are known: monosulfate structure containing the sulfate residue at the $^6$-position of N-acetylglucosamine and disulfate structure containing the sulfate residues at the 6-position of N-acetylglucosamine and that of galactose. The disulfate structure is more frequent in aggrecan.

Because, as described above, chondroitin sulfate contains carboxyl group and sulfate group and keratan sulfate contains sulfate group, aggrecan can retain a large amount of water. In addition, owing to mutual repulsion of these negative charges, the glycosaminoglycan chain tends to assume a loose coil form. Aggrecan, even when present alone, is a hydrated molecule which occupies a large space because of the property of its glycosaminoglycan chain, and, in the cartilage matrix, it aggregates with hyaluronan accompanied with the link protein to form a huge hydrated gel. This aggregate fills the interspace of type II collagen skeleton, so that the cartilage can function as a characteristic elastic body.

It has been reported that cartilage destruction associated with arthritis begins with degradation of aggrecan, and cleavage of aggrecan occurs mainly in the region between the G1 and G2 domains irrespective of the type of arthritis. Decomposed aggrecan of which G1 has been deprived of is incapable of binding hyaluronan in the matrix, and therefore is ready to be released into synovial fluid from the loosened cartilage. Thus the amount and quality of aggrecan and its degradation products is an important source of information on cartilage destruction.

Hyaluronan is outlined in the following:

Hyaluronan is a glycosaminoglycan consisting of repeating units of disaccharide consisting of N-acetylglucosamine and glucuronic acid, and though its concentration in the cartilage matrix is low, it has an important function in formation of proteoglycan aggregate as described above. In synovial fluid, it constitutes a main component present at the concentration of 2 to 3 mg/ml and is produced by synovial cells. The molecular weight of hyaluronan in synovial fluid is as large as several millions, so that hyaluronan occupies a larger space than other components do and retains a large amount of water inside the molecule. At the concentration in synovial fluid, hyaluronan molecules overlap each other, which contributes to the viscosity necessary for synovial fluid. That is, the molecular weight and the concentration of hyaluronan in synovial fluid are closely related to the characteristic viscosity of synovial fluid.

From these points of view, the relation between the concentration of aggrecan or glycosaminoglycan in the body fluid, such as synovial fluid and blood, and the type of the joint disease has been investigated. The concentration of such a marker molecule in synovial fluid is markedly increased in some types of arthritis, such as gout or traumatic arthritis (TA), where cartilage destruction proceeds rapidly, whereas the change in the concentration of a marker molecule in synovial fluid or blood is not very obvious in other types of arthritis, such as osteoarthritis (OA) and rheumatoid arthritis (RA), where cartilage destruction proceeds slowly so that the cartilage matrix components are released gradually.

This may be explained as follows:

The concentration and the total amount (concentration multiplied by the amount of synovial fluid) of a marker molecule in synovial fluid vary according not only to the extent of cartilage destruction but also to the amount of the cartilage, the rate of elimination of degradation products from the joint cavity, and the amount of plasma components transferred into synovial fluid. An extreme example is the case of rheumatoid arthritis at the terminal stage where there is little joint cartilage. It is no wonder that the concentration of aggrecan or glycosaminoglycan in synovial fluid in such a case is lower than that in synovial fluid in a normal joint.

For exclusion of the effect of these factors to know the pathological state of arthritis as exactly as possible, it is essential to determine the extent of degradation or denaturation of marker molecules in synovial fluid or in serum. The inventors found that a normal joint and a pathological joint can be differentiated from each other based on the proportion of normal aggrecan capable of forming an aggregate with hyaluronan in comparison with that of other proteoglycans, and that the type of arthritis can be identified based on comparison of the proportion of normal aggrecan with that of other proteoglycans.

Normal aggrecan which contains the hyaluronan binding region (G1 domain) forms an aggregate with hyaluronan in synovial fluid, and this aggregate-forming ability is a useful index of the extent of degradation or denaturation of aggrecan, because the proportion of normal aggrecan (aggregating form) in total proteoglycan is hardly influenced by any factor other than degradation of aggrecan. The inventors also found a convenient and exact method for assay of normal aggrecan capable of forming an aggregate with hyaluronan.

This invention utilizes the aggregate-forming ability of aggrecan as an index based on the fact that the proportion of normal aggrecan in total proteoglycan is hardly influenced by any factor other than degradation of aggrecan, and the fact that normal aggrecan containing the hyaluronan binding region can form an aggregate with hyaluronan also in synovial fluid.

First, this invention provides a method for assay of normal aggrecan which can bind hyaluronan. The method for assay in this invention is characterized in that only normal aggrecan is detected after separation of normal aggrecan capable of binding hyaluronan from proteoglycans incapable of binding hyaluronan.

The above-mentioned separation of normal aggrecan capable of binding hyaluronan from proteoglycans incapable of binding hyaluronan consists of the Process A and the Process B described in the following.

Process A: A process for degradation or removal of both hyaluronan bound to normal aggrecan and free hyaluronan in the specimen Process B: A process for separation of normal aggrecan from proteoglycans other than normal aggrecan wherein the treated specimen in the Process A is brought into contact with a solid phase capable of binding or adsorbing normal aggrecan so that only normal aggrecan in the specimen may be bound to or adsorbed on the solid phase.

Removal of hyaluronan in the specimen in the Process A is necessary because the method for assay in this invention is based on the hyaluronan-binding ability of normal aggrecan which is binding to hyaluronan in the specimen. For removal of hyaluronan in the specimen, enzymes are used which can degrade hyaluronan specifically or protein-denaturing agents.

Enzymes which can degrade hyaluronan include hyaluronan-degrading hyaluronidases and chondroitinase ABC ("Tosa Kogaku", pp.282–315, Aug. 1, 1992, published by Sangyo Chosakai Kabushiki Kaisha).

Hyaluronidases include an enzyme derived from a Streptomyces microorganism (e.g. *Streptomyces hyalurolyticus*) (EC4.2.2.1), an enzyme derived from medicinal leech (EC3.2.1.36), an enzyme derived from bovine testis (EC3.2.1.35), and an enzyme derived from a Streptococcus microorganism (e.g. *Streptococcus dysgalactie*), all of which are commercially available from Seikagaku Corporation.

Chondroitinase ABC (EC4.2.2.4) is exemplified by an enzyme derived from a Proteus microorganism (e.g. *Proteus vulgaris*) (marketed by Seikagaku Corporation). Protein-denaturing agents include 4M guanidine hydrochloride and 7M urea.

Conditions of the treatment in the Process A are not limited, though when an enzyme is used the treatment is carried out under the conditions taking the optimum temperature and the optimum pH for the enzyme into consideration. Use of hyaluronidase is preferable for the subsequent treatment.

When a protein-denaturing agent is used, an additional process may be required for separation of normal aggrecan from hyaluronan, such as density-gradient ultracentrifugation using cesium chloride, or glycerol, or other substance, or other appropriate method (see Zoku Seikagaku Jikken Koza, vol.4, Approach on Complex Carbohydrates, Glycolipid and Proteoglycan, Jan. 16, 1986, published by Tokyo Kagaku Dojin Kabushiki Kaisha, pp.253–263). When urea is used as a protein-denaturing agent, anion exchange chromatography may be used as an optional method (see ibid. pp.265–275). Then the normal aggrecan fraction thus separated is subjected to dilution or dialysis for reduction of the concentration of the concomitantly present protein-denaturing agent, or the protein-denaturing agent is removed. Reduction to a concentration below 0.4 M for guanidine hydrochloride and below 1.0 M for urea is enough for binding the normal aggrecan to the solid phase in the Process B.

The solid phase used in the Process B should be able to bind or adsorb specifically normal aggrecan capable of binding hyaluronan. Such a solid phase is exemplified by the one where hyaluronan has been immobilized. In the concrete, hyaluronan can be immobilized with a general method for preparation of an immobilized enzyme, such as covalent bonding method, physical adsorption method, etc. [see "Koteika Koso", Mar. 20, 1975, published by Kodansha Kabushiki Kaisha, pp.9–751].

For example, hyaluronan can be immobilized through the covalent bonding between the functional groups of hyaluronan (hydroxyl groups and carboxyl groups) and those of the solid phase (hydroxyl groups, carboxyl groups, amino groups, etc.) in the presence of a condensing agent (e.g. a water-soluble carbodiimide (WSC) such as 1-ethyl-3-(3-dimethylaminopropyl)carbodiimide, or dicyclohexylcarbodiimide (DCC), or the like). As the solid phase, are preferable carriers composed of polystyrene, cellulose, glass, etc. having functional groups such as amino group (microplate for immunological assay, support used for chromatography, etc.). Microplate for immunological assay is more preferable in view of convenience and high sensitivity.

In the Process B, the specimen treated as described in the Process A is first brought into contact with the above-mentioned solid phase, followed by separation of the specimen from the solid phase (by decantation, filtration, centrifugation, etc.) and, as required, washing, so that proteoglycans other than normal aggrecan are removed from the solid phase, and normal aggrecan bound to the solid phase is detected.

It is preferable that a reagent for stabilization of the binding or adsorption of normal aggrecan to hyaluronan is used concomitantly when the specimen is brought into contact with the above-mentioned solid phase. The reagents for stabilization include link protein and the like, which is present preferably at the concentration of 100 ng/ml to 100 $\mu$g/ml.

The link protein obtained by a prior art method is usable: such prior art method is exemplified by the cesium chloride sedimentation equilibrium centrifugation described in Zoku Seikagaku Jikken Koza, Vol.4, Approach on Complex Carbohydrates, II, pp.253–263, Jan. 16, 1986, published by Tokyo Kagaku Dojin Kabushiki Kaisha.

Separation of the above-mentioned normal aggrecan capable of binding hyaluronan from proteoglycans incapable of binding hyaluronan is also performed by separation of the aggregate of normal aggrecan bound to hyaluronan in the specimen from proteoglycans incapable of binding hyaluronan based on the difference in molecular weight. For the separation based on the difference in molecular weight may be used a filter apparatus equipped with a membrane filter which can collect the aggregate of normal aggrecan bound to hyaluronan by filtration, or an apparatus for gel filtration.

When the specimen is synovial fluid obtained from the joint to be examined, normal aggrecan in the specimen is bound to hyaluronan to form a giant molecule having a molecular weight of several millions or more. Such a giant molecule can be retained on a membrane filter of an appropriate pore size (0.1–0.45 $\mu$m, preferably about 0.2 $\mu$m), whereas aggrecan incapable of binding hyaluronan passes through the membrane filter. Various membrane filters may be used for this purpose, and membrane filters with little non-specific adsorption, such as those made of teflon, are preferable.

Such a membrane filter is placed in an appropriate filter apparatus, where the specimen is subjected to pressurized or centrifugal filtration. When the specimen is a body fluid other than synovial fluid, addition of hyaluronan of a molecular weight of several hundred thousands to the specimen is necessary for formation of an aggregate of normal aggrecan bound to hyaluronan (called hyaluronan-aggrecan aggregate sometimes hereinafter).

In the method for assay in this invention, normal aggrecan thus separated is detected by a means for detection of proteoglycan. Means employed for detection of proteoglycan are those for specific detection of keratan sulfate or chondroitin sulfate bound to normal aggrecan or of the core-protein of normal aggrecan.

Namely, this invention provides the method for assay of normal aggrecan (called "Assay Method 1" hereinafter) consisting of the Processes A, B, and C described in the following.

Assay Method 1

Process A: A process for degradation or removal of both hyaluronan bound to normal aggrecan and free hyaluronan in the specimen Process B: A process for separation of normal aggrecan from proteoglycans other than normal aggrecan wherein the treated specimen in the Process A is brought into contact with a solid phase capable of binding or adsorbing normal aggrecan so that only normal aggrecan in the specimen may be bound to or adsorbed on the solid phase, and Process C: A process for detection of normal aggrecan bound to or adsorbed on the solid phase.

It is preferable to use concomitantly a reagent for stabilization of adsorption of normal aggrecan onto the solid phase when the specimen is brought into contact with the solid phase in the Process B.

Normal aggrecan is bound to hyaluronan on the solid phase via the hyaluronan binding region (G1 domain). Normal aggrecan bound to or adsorbed on the solid phase via the hyaluronan is detected by various means for detection of proteoglycan. For example, it is detected by staining the sulfated glycosaminoglycan bound to normal aggrecan with a dye such as 1,9-dimethylmethylene blue. It is also detected by immunological quantification (immunoassay) or by immunological staining with an antibody specific to the sulfated glycosaminoglycan bound to normal aggrecan, such as chondroitin sulfate or keratan sulfate, or by high performance liquid chromatography. Antibodies to the core-protein of normal aggrecan are also usable.

This invention intends to quantify normal aggrecan that still possesses at least the hyaluronan binding region (G1 domain), the G2 domain, and glycosaminoglycan. Therefore, for detection of normal aggrecan bound to or adsorbed on the solid phase via the hyaluronan binding region, the method for detection of glycosaminoglycan such as keratan sulfate or chondroitin sulfate is preferable. It is preferable to use an antibody to chondroitin sulfate or keratan sulfate to ensure convenience and sufficient sensitivity.

As an antibody to chondroitin sulfate or keratan sulfate, any of those that are specific to such a sulfated glycosaminoglycan bound to normal aggrecan is usable.

Various monoclonal antibodies to chondroitin sulfate are known, some of which are generally available (Shin Seikagaku Jikken Koza, Vol.3, Carbohydrates II, pp.385–391, Apr. 15, 1991, published by Tokyo Kagaku Dojin Kabushiki Kaisha; Antibodies named CS-56, MO-225, MC21C, S54C, 3B3).

Of these, MO-225 ("Anti-chondroitin sulfate (Type-D)" is commercially available from Seikagaku Corporation (Japanese Published Unexamined Patent Application (KOKAI TOKKYO KOHO) No.137695/88).

Monoclonal antibodies to keratan sulfate are known and generally available (Shin Seikagaku Jikken Koza, Vol.3, Carbohydrates II, pp.391–393, Apr. 15, 1991, published by Tokyo Kagaku Dojin Kabushiki Kaisha; Antibodies named 1/20/5D4 or 5D4). The antibody 5D4 is commercially available from Seikagaku Corporation (J. Biol. Chem., 258, 8848 (1983), Japanese Published Unexamined Patent Application (KOKAI TOKKYO KOHO) No.224065/85).

This invention also provides the method for assay of normal aggrecan consisting of the Process A and the Process B as described below ("Assay Method 2" hereinafter).

Assay Method 2

Process A: A process for separation of the aggregate of normal aggrecan bound to hyaluronan from proteoglycan incapable of binding hyaluronan in the specimen, based on the difference in molecular weight, and Process B: A process for detection of hyaluronan-aggrecan aggregate collected on the membrane filter.

The above-mentioned hyaluronan-aggrecan aggregate retained on the membrane filter is detected with various means. For example, sulfated glycosaminoglycan is detected with 1,9-dimethylmethylene blue in a similar manner as described above.

Sulfated glycosaminoglycan such as chondroitin sulfate or keratan sulfate is also detected by using a specific antibody or by high performance liquid chromatography. In addition, an antibody to the core-protein of normal aggrecan is also usable.

This invention intends to quantify normal aggrecan that possesses at least the hyaluronan binding region (G1 domain), the G2 domain, and glycosaminoglycan. Therefore, for detection of normal aggrecan bound to or adsorbed on the solid phase via the hyaluronan binding region, the method for detection of glycosaminoglycan is preferable. It is preferable to use an antibody to chondroitin sulfate or keratan sulfate to ensure convenience and sufficient sensitivity.

The specimen is not limited, but preferably it is synovial fluid from the joint to be examined.

In the following, is explained the method used in this invention for detection of normal aggrecan bound to or adsorbed on the solid phase via the hyaluronan binding region by use of an antibody to chondroitin sulfate or keratan sulfate.

The core-protein of normal aggrecan has the hyaluronan binding region which binds hyaluronan specifically and reversibly. Keratan sulfate is a glycosaminoglycan covalently bound to the core-protein of normal aggrecan at multiple sites, and concentrates in the KS rich region near the hyaluronan binding region.

Several methods are known for immunoassay using the above-mentioned antibodies to quantify chondroitin sulfate and keratan sulfate in a biological specimen.

In the literature "Quantification of Keratan Sulfate in Blood as a Marker of Cartilage Catabolism" in the Arthritis and Rheumatism (Thonar et al, 1985, Vol.28, pp.1367–1376) is described the enzyme-linked-immunosorbent assay (ELISA) using an anti-keratan sulfate-specific monoclonal antibody for quantification of keratan sulfate in adult human serum.

The above-mentioned method for quantification of keratan sulfate is explained with an example in the following.

Process a: Hyaluronan is made bound to a solid phase to prepare a hyaluronan-immobilized solid phase, Process b: the specimen treated in a process for degradation or removal of both hyaluronan bound to normal aggrecan or of free hyaluronan in the specimen, and the link protein are brought into contact with the solid phase obtained in the Process a, followed by incubation so that free normal aggrecan is bound to hyaluronan which has been bound to the above-mentioned solid phase, Process c: the product of the Process b is brought into contact with a keratan sulfate-reactive antibody, so that this antibody is bound to the keratan sulfate of normal aggrecan which has been bound to hyaluronan bound to the above-mentioned solid phase, Process d: the above-mentioned antibody bound to the above-mentioned keratan sulfate is detected, and Process e: the amount of the antibody bound to the above-mentioned keratan sulfate is converted to the amount of normal aggrecan in the specimen.

The anti-keratan sulfate antibody, which has been bound to the solid phase (microplate etc.) in the Process c, may be detected in the Process d by use of a second antibody which is reactive with the antibody to be detected and has been labeled with an appropriate labeling substance such as an enzyme, radioisotope, fluorescent substance, biotin, avidine, etc.

For example, it the first antibody is a mouse anti-keratan sulfate monoclonal antibody, the labeled second antibody may be an anti-mouse immunoglobulin antibody bound to a labeling substance. For example, these second antibodies of Jackson Co. which are specific to immunoglobulins of various animal species and have been labeled with peroxidase, alkaline phosphatase, fluorescein isothiocyanate (FITC), 7-amino-4-methylcoumarin-3-acetate (AMCA), biotin, or the like, are easily commercially available from Seikagaku Corporation.

When the second antibody is a peroxidase-labeled one, the bonding between the first antibody bound to the solid phase and the second antibody is usually detected by a color reaction with peroxidase.

That is, hydrogen peroxide, the substrate of peroxidase, and a coloring substance (O-phenylenediamine, 3, 3', 5, 5'-tetramethylbenzidine) are used for the reaction, where the color intensity is proportional to the amount of peroxidase bound to the solid phase and the absorbance is determined at the wave-length suitable for the coloring substance used. When the solid phase is a microplate, the absorbance is determined with a microplate reader [e.g. Wellreader SK601 (Seikagaku Corporation), MR600 (Dynatec Co.) etc.].

The above-mentioned method for detection using the anti-keratan sulfate antibody is applicable also to detection using the anti-chondroitin sulfate antibody.

The present invention provides measurement kits used in the method for assay of normal aggrecan. Such kits are exemplified by a kit used in the Assay Method 1 described above (abbreviated as 'Measurement Kit 1' hereinafter) consisting of the reagents A, B, and C of the following composition.

Measurement Kit 1
A: A reagent for degradation or removal of both hyaluronan bound to normal aggrecan and free hyaluronan in the specimen,
B: A solid phase for specific binding or adsorption of normal aggrecan, and
C: A reagent for detection of normal aggrecan bound to or adsorbed on the solid phase described in B.

In the Measurement Kit 1, an additional reagent may be used for stabilization of the bond between normal aggrecan and hyaluronan or for stabilization of adsorption.

The above-mentioned B is a solid phase to bind or adsorb normal aggrecan in the specimen by bringing the specimen treated with the above-mentioned A into contact with the solid phase capable of binding or adsorbing normal aggrecan. The solid phase may be microplates and carriers for chromatography in which hyaluronan has been bound covalently or has been adsorbed physically so that normal aggrecan capable of binding hyaluronan in the specimen may be bound or adsorbed selectively. Microplates for immunoassay such as those for enzyme-linked immunosorbent assay (ELISA), are desirable for convenience and high sensitivity.

The above-mentioned reagents for stabilization include link protein and the like.

The above-mentioned Reagent C is a reagent for specific detection of keratan sulfate or chondroitin sulfate bound to normal aggrecan, or of the core-protein of normal aggrecan.

The present invention provides a measurement kit used in the Assay Method 2 (abbreviated 'Measurement Kit 2' hereinafter) consisting of the Apparatus A and Reagent B described below.

Measurement Kit 2
Apparatus A: An apparatus capable of fractionation based on molecular weight for separation of the aggregate of normal aggrecan bound to hyaluronan from proteoglycan incapable of binding hyaluronan, and Reagent B: A reagent for detection of normal aggrecan separated in the form of hyaluronan-normal aggrecan aggregate.

The above-mentioned Apparatus A is a filter apparatus equipped with a membrane filter which can collect the aggregate of normal aggrecan bound to hyaluronan.

The above-mentioned Reagent B is a reagent for specific detection of keratan sulfate or chondroitin sulfate bound to normal aggrecan or of the core protein of normal aggrecan.

The specimen is preferably synovial fluid from the joint to be examined.

The Apparatus A consists of a membrane filter and a filter apparatus for collection of normal aggrecan bound to hyaluronan in the specimen (hyaluronan-aggrecan aggregate) on the membrane filter. Normal aggrecan in the specimen is bound to hyaluronan to form a macromolecule having a molecular weight of several millions or more. This macromolecule can be retained on a membrane filter of a suitable pore size (0.1 to 0.45 $\mu$m, preferably about 0.2 $\mu$m), whereas aggrecan incapable of binding hyaluronan passes through the membrane filter. Various kinds of membrane filter are usable for this purpose, and those with little non-specific adsorption, such as those made of teflon, are preferable. Such a membrane filter is placed in a suitable filter apparatus, and a specimen is filtered through the membrane filter under a suitable pressure or by centrifugal force. For filtration of a body fluid other than synovial fluid, addition of hyaluronan of a molecular weight of several hundred thousands or more to the specimen is necessary so that hyaluronan-aggrecan aggregate may be formed.

The present invention provides a method for evaluation of information on the joint, by making use of the above-mentioned assay methods and the measurement kits. When the specimen is synovial fluid, this invention affords information on the metabolism of the joint cartilage matrix.

Proteoglycans present in normal synovial fluid have not yet been degraded very much, in which normal aggrecan capable of binding hyaluronan accounts for about 38%. Under pathological conditions such as osteoarthritis and rheumatoid arthritis, normal aggrecan capable of aggregating accounts for as low as about 18% of proteoglycans in synovial fluid. The difference in the percentage may reflect exactly the difference in the extent of degradation of the cartilage matrix.

The absolute amount and the percentage of normal aggrecan and other proteoglycans were determined in synovial fluid from normal subjects, and from patients of osteoarthritis, rheumatoid arthritis, and traumatic arthritis (TA): the values thus obtained represent characteristically the pathological conditions, and therefore these molecules are expected to be useful biochemical diagnostic markers of the pathological conditions. In the concrete, the concentration of normal aggrecan and the percentage of normal aggrecan in total proteoglycan are useful for differentiation of normal joints from pathological joints, for understanding of the pathological conditions, such as type of the joint disease and estimation of prognosis, and for evaluation of the effect of therapies.

In the following, is described relation between arthritis and glycosaminoglycan and proteoglycans in synovial fluid and in serum.

As described above, when the cartilage has been destructed in arthritis, degradation products of proteoglycan are released from the cartilage matrix into synovial fluid and then into blood. According to recent reports on glycosaminoglycan, a proteoglycan of which amount changes along with progress of arthritis, marker molecules determined are keratan sulfate, chondroitin sulfate, and sulfated glycosaminoglycan (S-GAG) which is the sum of the former two, and also proteoglycan fragments. In the following changes of marker molecules, i.e. keratan sulfate, chondroitin sulfate, S-GAG, and proteoglycan fragments, are outlined.

1. Keratan sulfate

A specific monoclonal antibody is commercially available, so that this marker molecule is being extensively studied with ELISA or radioimmunoassay (RIA). Its concentration in synovial fluid is increased markedly in gout or reactive arthritis. Its concentration in blood is said to be increased in osteoarthritis (OA) and rheumatoid arthritis (RA) in some reports, or to show little change in other reports.

2. Chondroitin sulfate

The result of determination with HPLC of unsaturated disaccharides produced by digestion with chondroitinase ABC has been reported. The concentration of C6S among chondroitin sulfate isomers is, like the concentration of keratan sulfate, remarkably high in traumatic arthritis, probably reflecting rapid destruction of the cartilage. The C4S concentration in synovial fluid is higher in rheumatoid arthritis than in osteoarthritis, and the C6S/C4S ratio is lower in rheumatoid arthritis than in osteoarthritis and traumatic arthritis. C4S may be of the synovial membrane or serum origin, possibly reflecting synovitis in rheumatoid arthritis.

3. Sulfated glycosaminoglycan (S-GAG)

It may well be assumed that its concentration represents the sum of the concentration of chondroitin sulfate and that of keratan sulfate in synovial fluid. The concentration is determined conveniently with a dye (1,9-dimethylmethylelene blue: DMB) which can determine S-GAG concentration specifically. The concentration in synovial fluid is markedly elevated in gout and reactive arthritis, but not evidently elevated in osteoarthritis or in rheumatoid arthritis.

4. Proteoglycan fragments

The concentration of each fragment is determined with an antibody specific to each fragment of aggrecan for clarification of metabolism, degradation, and mechanism of release of aggrecan. The concentration of the glycosaminoglycan-rich fragment in synovial fluid may change similarly to that of S-GAG. The concentration of the hyaluronan-binding region is low in the initial stage of rheumatoid arthritis and increased along with the progress of the disease. This is considered to be due to the fact that the hyaluronan-binding region is retained in the joint matrix in the initial stage of cartilage destruction.

5. Summary

In gout or traumatic arthritis where cartilage destruction makes a rapid progress, markedly elevated concentrations of the above-mentioned marker molecules in synovial fluid are noted. In osteoarthritis or rheumatoid arthritis where cartilage destruction makes a slow progress, the concentrations of the marker molecules in synovial fluid of serum do not change very obviously because the cartilage components are released gradually.

For understanding the state of arthritis as exactly as possible, it is necessary to know the extent of degradation or degeneration of the marker molecules in synovial fluid or serum.

The method for evaluation of information on a joint in the present invention is characterized in that the information on the amount of normal aggrecan in the specimen is obtained, and the information thus detected is evaluated to be one derived from a pathological joint if a significant difference is note and is evaluated to be the one derived from a normal joint if a significant difference is not found, when the information is compared with the previously obtained information on the amount of normal aggrecan and the amount of total proteoglycan in synovial fluid from a normal joint.

The information on the amount of normal aggrecan in the specimen is obtained by determination of the concentration of normal aggrecan in the specimen with the above-mentioned 'Assay Method 1' or 'Assay Method 2' and additionally by determination of the concentration of total proteoglycan so that the percentage of normal aggrecan in total proteoglycan may be calculated.

Presence of the above-mentioned significant difference means that the calculated percentage of normal aggrecan in total proteoglycan in the specimen is significantly lower than the previously determined percentage of normal aggrecan in total proteoglycan in synovial fluid from a normal joint.

When such a significant difference is found, the information is considered to indicate a pathological state selected among the group of diseases including osteoarthritis, rheumatoid arthritis, traumatic arthritis, and gout.

The above-mentioned information on the amount of normal aggrecan in the specimen is obtained by determination of the concentration of normal aggrecan in the specimen with the above-mentioned Assay Method 1 or Assay Method 2 and additionally by determination of the concentration of total proteoglycan in the specimen, followed by calculation of the concentration of proteoglycan other than normal aggrecan from the difference between the concentration of total proteoglycan and that of normal aggrecan.

Presence of the above-mentioned significant difference means that the concentration of normal aggrecan in the specimen is significantly lower than the previously determined concentration of normal aggrecan in synovial fluid from a normal joint and at the same time the concentration of proteoglycan other than normal aggrecan in the specimen is not significantly different from the previously determined concentration of proteoglycan other than normal aggrecan in synovial fluid from a normal joint. Presence of a significant difference is considered to indicate osteoarthritis, rheumatoid arthritis, and the like where cartilage destruction makes a slow progress, and absence of a significant difference is considered to indicate a normal joint.

The above-mentioned significant difference is noted in various conditions. A significant difference is found, for example, in cases where the concentration of normal aggrecan in the specimen is not different from the previously determined concentration of normal aggrecan in synovial fluid from a normal joint and at the same time the concentration of proteoglycan other than normal aggrecan in the specimen is significantly higher than the previously determined concentration of proteoglycan other than normal aggrecan in synovial fluid from a normal joint. Presence of the above-mentioned significant difference is considered to be an information on a type of arthritis where cartilage destruction proceeds rapidly, such as traumatic arthritis or gout, while absence of significant difference is considered to be an information on a normal joint.

The above-mentioned specimen is preferably synovial fluid from the joint to be examined.

BEST EMBODIMENTS OF THE INVENTION

The present invention will be more clearly understood with reference to the following Examples. The present invention is not limited at all by these Examples.

EXAMPLE 1

An example of determination of the concentration of normal aggrecan in synovial fluid with the Assay Method 1 is described.

(1) A process for degradation or removal of both hyaluronan bound to normal aggrecan and of free hyaluronan in the specimen About 10 mg of synovial fluid of a normal subject or of a patient with osteoarthritis, rheumatoid arthritis, or traumatic arthritis was exactly weighed and diluted ten times with distilled water. To 80 μl of the diluted fluid; were added 5 TRU (Turbidity Reducing Unit)/50 μl of hyaluronidase derived from a micro-organism of Streptomyces sp. (Seikagaku Corporation), 80 μl of 100 mM sodium acetate buffer (pH 6.0), and 80 μl of a solution of a protease inhibitor (100 mM 6-aminocaproic acid, 10 mM sodium ethylenediamine-tetraacetate, 10 mM N-ethyl maleimide, 10 mM phenylmethanesulfonyl fluoride), followed by digestion at 40° C. for 2 hours. With this treatment, hyaluronan in the specimen was degraded to tetra- or hexa-saccharides, losing the normal aggrecan-binding ability.

(2) A process where the specimen treated as described above is brought into contact with a solid phase capable of binding or adsorbing normal aggrecan so that normal aggrecan in the specimen is bound to or adsorbed on the solid phase To the treated specimen was added a suitable amount of a hyaluronidase-inhibitor (mercuric chloride, potassium ferricyanide, etc.), and a portion of the specimen thus treated was added to a 96-well plate (microplate) to which hyaluronan had been bound covalently. In this Example was used Aminoplate manufactured by Sumitomo Bakelite Co. to which hyaluronan had been bound covalently by use of 1-ethyl-3-(3-dimethylaminopropyl)carbodiimide. After incubation at 15° C. for 4 hours, the plate was washed sufficiently with a Well-plate-washing machine.

(3) A process for detection of normal aggrecan bound to or adsorbed on the solid phase A solution of an anti-keratan sulfate monoclonal antibody (Clone name: 5D4, Subclass $IgG_1$, manufactured by Seikagaku Corporation ) was added to the well and kept still at 4° C. for 2 hours. The well-plate was washed, to which peroxidase-labeled anti-mouse IgG antibody (manufactured by Seikagaku Corporation) was added and kept still at 4° C. for further 2 hours. After washing and coloration with O-phenylenediamine according to the conventional method, the absorbance was determined with a Well-reader (SK60) (Seikagaku Corporation). The concentration of normal aggrecan in synovial fluid was calculated from the calibration curve prepared independently using bovine aggrecan (manufactured by Seikagaku Corporation).

Addition of 1 μg of link protein prepared separately to the specimen when the specimen is brought into contact with the above-mentioned solid phase with a method similar to that described above gave results similar to those described below. The link protein preparation used was obtained with the cesium chloride-sedimentation equilibrium centrifugation described in the Zoku Seikagaku Jikken Koza, Vol. 4, Approach on Complex Carbohydrates II, pp.253–263, Jan. 16, 1986, published by Tokyo Kagaku Dojin Kabushiki Kaisha.

(4) Results

Table 1 lists the concentration of normal aggrecan, the concentration of proteoglycan (PG) other than normal aggrecan, and the percentage of normal aggrecan in total proteoglycan in human synovial fluid determined with the above-mentioned Methods.

The concentration of total proteoglycan was determined by making use of an anti-keratan sulfate monoclonal antibody and bovine aggrecan as the standard, according to the method reported earlier (Ratcliffe, A., et al.: Ann. Rheum. Dis., 47, 826 (1988)). The concentration of proteoglycan other than normal aggrecan was calculated by subtraction of the concentration of normal aggrecan from that of total proteoglycan.

TABLE 1

| Origin of specimen | normal | OA | RA | TA |
|---|---|---|---|---|
| Nos. of patients | 4 | 9 | 10 | 10 |
| Concentration of normal aggrecan (μg/ml) | 33.2 ± 8.26 | 17.4 ± 7.42** | 3.84 ± 1.19** | 23.4 ± 16.2 |
| Concentration of PG other than normal aggrecan (μg/ml) | 72.8 ± 14.1 | 94.8 ± 32.6 | 51.6 ± 52.6 | 172 ± 107* |
| Percentage of normal aggrecan (%) | 37.5 ± 15.1 | 17.5 ± 6.68** | 12.9 ± 8.77** | 12.9 ± 5.26** |

Values are means ± standard deviation.
Significance test was made on the difference from the normal values.
*$p < 0.05$
**$p < 0.01$ Though the number of subjects was as small as 4 to 10, the percentage of normal aggrecan was significantly lower in pathological joints, suggesting that aggrecan has been degraded in these joints. The concentration of normal aggrecan was significantly lower in osteoarthritis (OA) or rheumatoid arthritis (RA) but was not different in traumatic arthritis (TA) as compared with that in normal subjects. However the concentration of proteoglycan other than normal aggrecan was characteristically elevated in traumatic arthritis (TA) Thus determination of the concentration and the percentage of normal aggrecan enables differentiation of joint diseases and provides information on cartilage destruction.

The concentration of C6S, considered to be a marker molecule, was significantly higher in traumatic arthritis than in normal subjects, though it was not different in osteoarthritis from that in normal subjects and rather lower in rheumatoid arthritis.

With the Assay Method 2 on the same specimens also give similar results.

INDUSTRIAL APPLICABILITY

The present invention is useful for biochemical diagnosis of joint diseases in the field of orthopedics. Determination of the concentration of normal aggrecan and the percentage of normal aggrecan in total proteoglycan is usable for differentiation between a normal joint and a pathological joint, for understanding of the pathological conditions, such as type of the joint disease and estimation of the prognosis, and also for evaluation of the effect of therapies.

SUMMARY OF THE INVENTION

A method for assay of normal aggrecan wherein normal aggrecan capable of binding hyaluronan is separated from proteoglycan incapable of binding hyaluronan so that only normal aggrecan can be detected, and a measurement kit used for the assay. Normal aggrecan thus separated is detected with a means for detection of proteoglycan. The specimen is preferably synovial fluid from the joint to be examined. A method for evaluation of information on a joint wherein information on the amount of normal aggrecan and the amount of total proteoglycan in the specimen is detected with said method and said measurement kit for assay of normal aggrecan, such information is compared with the previously obtained information on the amount of said substances in synovial fluid from a normal joint, and the information is evaluated to be the one derived from a normal joint or a pathological joint based on the absence or presence of significant difference. Presence of significant difference is considered to indicate a disease selected among a group of diseases consisting of osteoarthritis, rheumatoid arthritis, traumatic arthritis, and gout.

This invention is usable for biochemical diagnosis of joint diseases in the field of orthopedics. Determination of the concentration of normal aggrecan and the percentage of normal aggrecan in total proteoglycan is useful for differentiation between a normal joint and a pathological joint, for understanding of the pathological conditions, such as the type of the joint disease and estimation of the prognosis, and also for evaluation of the effect of therapies.

What is claimed is:

1. A method of determining the ratio of normal aggrecan to other proteoglycans in a joint and the difference of concentration between normal aggrecan and other proteoglycans in a joint, comprising steps of:

taking synovial fluid from a joint which is suspected to have arthritis;

measuring concentration A of normal aggrecan in said synovial fluid;

measuring concentration B of total proteoglycan including said normal aggrecan and other proteoglycan in said synovial fluid; and either one of calculating the ratio of said concentration A of normal aggrecan to said concentration B of total proteoglycan, i.e. A/B; or comparing said concentration A of normal aggrecan with the difference between said concentration B of total proteoglycan and said concentration A of normal aggrecan, i.e. B−A.

2. A method of determining the concentration of normal aggrecan in a joint, comprising steps of:

a) taking synovial fluid from a joint which is suspected to have arthritis;

b) degrading or removing hyaluronan bound to normal aggrecan and free hyaluronan in said synovial fluid;

c) contacting said synovial fluid treated by step b) with a solid phase having hyaluronan bound on said solid phase, thereby binding or adsorbing to said solid phase only normal aggrecan capable of binding to hyaluronan without binding or adsorbing to said solid phase proteoglycan, including aggrecan which has lost ability of binding to hyaluronan, other than normal aggrecan;

d) separating said solid phase from said synovial fluid treated by step c);

e) detecting normal aggrecan separated and bound or adsorbed to said solid phase in step d) by utilizing means for detecting keratan sulfate, chondroitin sulfate, or proteoglycan; and f) determining concentration of normal aggrecan in synovial fluid obtained in step a) from said normal aggrecan detected in step e).

3. A method of determining the concentration of normal aggrecan in a joint as defined in claim 2, wherein, in step c), a link protein is added to said synovial fluid to stabilize the binding or adsorption of normal aggrecan to hyaluronan.

4. A method of determining the concentration of normal aggrecan in a joint as defined in claim 2, further comprising steps of:

g) measuring concentration B of total proteoglycan, including both normal aggrecan and other proteoglycan, in said synovial fluid obtained in step a); and h) calculating ratio of said concentration A of normal aggrecan obtained in step f) to said concentration B of total proteoglycan obtained in step g), i.e., A/B.

5. A method of diagnosis of arthritis comprising steps of:

a) taking synovial fluid from a joint which is suspected to have arthritis;

b) degrading or removing hyaluronan bound to normal aggrecan and free hyaluronan in said synovial fluid;

c) contacting said synovial fluid treated by step b) with a solid phase having hyaluronan bound on said solid phase, thereby binding or adsorbing to said solid phase only normal aggrecan capable of binding to hyaluronan without binding or adsorbing to said solid phase proteoglycan, including aggrecan which has lost ability of binding to hyaluronan, other than normal aggrecan;

d) separating said solid phase from said synovial fluid treated by step c);

e) detecting normal aggrecan separated and bound or adsorbed to said solid phase in step d) by utilizing means for detecting keratan sulfate, chondroitin sulfate, or proteoglycan;

f) determining concentration A of normal aggrecan in synovial fluid obtained in step a) from said normal aggrecan detected in step e);

g) measuring concentration B of total proteoglycan, including both normal aggrecan and other proteoglycan, in said synovial fluid obtained in step a);

h) calculating ratio of said concentration A of normal aggrecan obtained in step f) to said concentration B of total proteoglycan obtained in step g), i.e., A/B; and i) diagnosing as an arthritis when said ratio A/B significantly decreases in comparison with corresponding value measured regarding synovial fluid from a normal joint.

6. A method of diagnosis of arthritis comprising steps of:

a) taking synovial fluid from a joint which is suspected to have arthritis;

b) degrading or removing hyaluronan bound to normal aggrecan and free hyaluronan in said synovial fluid;

c) contacting said synovial fluid treated by step b) with a solid phase having hyaluronan bound on said solid phase, thereby binding or adsorbing to said solid phase only normal aggrecan capable of binding to hyaluronan without binding or adsorbing to said solid phase proteoglycan, including aggrecan which has lost ability of binding to hyaluronan, other than normal aggrecan;

d) separating said solid phase from said synovial fluid treated by step c);

e) detecting normal aggrecan separated and bound or adsorbed to said solid phase in step d) by utilizing means for detecting keratan sulfate, chondroitin sulfate, or proteoglycan;

f) determining concentration A of normal aggrecan in synovial fluid obtained in step a) from said normal aggrecan detected in step e);

g) measuring concentration B of total proteoglycan, including both normal aggrecan and other proteoglycan, in said synovial fluid obtained in step a);

h) calculating difference, i.e. concentration B−A, between said concentration B of total proteoglycan obtained in step g) and said concentration A of normal aggrecan obtained in step f;

i) comparing said concentration A of normal aggrecan and said concentration B−A of proteoglycan other than normal aggrecan with corresponding value measured regarding synovial fluid from a normal joint; and j) diagnosing as an arthritis when there is significant variation of A or B−A from the normal value of A or B−A, respectively.

7. A method of diagnosis of arthritis comprising steps of:

a) taking synovial fluid from a joint which is suspected to have arthritis;

b) degrading or removing hyaluronan bound to normal aggrecan and free hyaluronan in said synovial fluid;

c) contacting said synovial fluid treated by step b) with a solid phase having hyaluronan bound on said solid phase, thereby binding or adsorbing to said solid phase only normal aggrecan capable of binding to hyaluronan without binding or adsorbing to said solid phase proteoglycan, including aggrecan which has lost ability of binding to hyaluronan, other than normal aggrecan;

d) separating said solid phase from said synovial fluid treated by step c);

e) detecting normal aggrecan separated and bound or adsorbed to said solid phase in step d) by utilizing means for detecting keratan sulfate, chondroitin sulfate, or proteoglycan;

f) determining concentration A of normal aggrecan in synovial fluid obtained in step a) from said normal aggrecan detected in step e);

g) measuring concentration B of total proteoglycan, including both normal aggrecan and other proteoglycan, in said synovial fluid obtained in step a);

h) calculating difference, i.e. concentration B−A, between said concentration B of total proteoglycan obtained in step g) and said concentration A of normal aggrecan obtained in step f);

i) comparing said concentration A of normal aggrecan and said concentration B−A of proteoglycan other than normal aggrecan with corresponding values, A' and B'−A', which respectively correspond to values A and B−A measured regarding synovial fluid from normal joint;

j) diagnosing as an arthritis with slow cartilage destruction when A is significantly low but there is no significant difference in B−A; and k) diagnosing as an arthritis with rapid cartilage destruction when there is no significant difference in A but B−A is significantly high.

* * * * *